United States Patent [19]
Goddard et al.

[11] Patent Number: 5,064,851
[45] Date of Patent: Nov. 12, 1991

[54] 3-(1-SUBSTITUTED-PYRAZOYL)-2-OXINDOLE DERIVATIVES, COMPOSITIONS AND USE

[75] Inventors: Carl J. Goddard, Groton; Gary R. Schulte, Stonington, both of Conn.

[73] Assignee: Pfizer Inc., New York, N.Y.

[21] Appl. No.: 557,265

[22] Filed: Jul. 24, 1990

[51] Int. Cl.$^5$ .................. A61K 31/415; C07D 403/06
[52] U.S. Cl. ...................... 514/406; 514/80; 514/825; 514/863; 514/885; 548/119; 548/374
[58] Field of Search .................. 548/119, 374; 514/80, 514/406, 825, 863, 885

[56] References Cited
U.S. PATENT DOCUMENTS

| | | | |
|---|---|---|---|
| 4,556,672 | 12/1985 | Kadin | 514/414 |
| 4,569,942 | 2/1986 | Kadin | 514/414 |
| 4,861,794 | 8/1989 | Otterness | 514/414 |

Primary Examiner—Robert W. Ramsuer
Attorney, Agent, or Firm—Peter C. Richardson; J. Trevor Lumb; Gregg C. Benson

[57] ABSTRACT

This invention relates to novel 3-(1-substituted-pyrazoyl)-2-oxindole derivatives which are inhibitors of prostaglandin $H_2$ synthease, 5-lipoxygenase and interleukin-1 biosynthesis. The compounds of the invention are useful as inhibitors of prostaglandin $H_2$ synthase and interleukin-1 biosynthesis, per se, and as analgesic, anti-inflammatory and antiarthritic agents in the treatment of chronic inflammatory diseases. This invention also relates to pharmaceutical compositions comprising said 3-(1-substituted-pyrazoyl-2-oxindole derivatives; to methods of inhibiting prostaglandin $H_2$ synthase and biosynthesis of interleukin-1; and to treating chronic inflammatory diseases in a mammal with said compounds. Further, this invention relates to certain novel compounds useful as intermediates in the preparation of the 3-(1-substituted-pyrazoyl-2-oxindole derivatives of this invention and to a process for the preparation of the 3-(1-substituted-pyrazoyl)-2-oxindole derivatives.

28 Claims, No Drawings

3-(1-SUBSTITUTED-PYRAZOYL)-2-OXINDOLE DERIVATIVES, COMPOSITIONS AND USE

TECHNICAL FIELD

This invention relates to novel 3-(1-substituted-pyrazoyl)-2-oxindole derivatives which are inhibitors of prostaglandin H$_2$ synthase, 5-lipoxygenase and interleukin-1 biosynthesis. The compounds of the invention are useful as inhibitors of prostaglandin H$_2$ synthase and interleukin-1 biosynthesis, per se, and as analgesic, antiinflammatory and antiarthritic agents in the treatment of chronic inflammatory diseases. This invention also relates to pharmaceutical compositions comprising said 3-(1-substitutedpyrazoyl)-2-oxindole derivatives; to methods of inhibiting prostaglandin H$_2$ synthase and biosynthesis of interleukin-1; and to treating chronic inflammatory diseases in a mammal with said compounds. Further, this invention relates to certain novel compounds useful as intermediates in the preparation of the 3-(1-substitutedpyrazoyl)-2-oxindole derivatives of this invention and to a process for the preparation of the 3-(1-substitutedpyrazoyl)-2-oxindole derivatives.

BACKGROUND ART

U.S. Pat. No. 4,569,942 discloses certain 2-oxindole-1-carboxamides of the formula

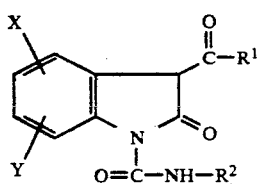

wherein, inter alia, X is H, fluoro, chloro, bromo, (C$_1$-C$_4$)alkyl, (C$_3$-C$_7$)cycloalkyl, (C$_1$C$_4$)alkoxy, (C$_1$-C$_4$)alkylthio, trifluoromethyl, (C$_1$C$_4$)alkylsulfinyl, (C$_1$C$_4$)alkylsulfonyl, nitro, phenyl, (C$_2$-C$_4$)-alkanoyl, benzoyl, thenoyl, (C$_1$C$_4$)alkanamido, benzamido or N,N-dialkylsulfamoyl having 1 to 3 carbons in each of said alkyls; Y is, H, fluoro, chloro, bromo, (C$_1$C$_4$)alkyl, (C$_3$-C$_7$)cycloalkyl, (C$_1$C$_4$)alkoxy, (C$_1$C$_4$)alkylthio and trifluoromethyl; R$^1$ is (C$_1$-C$_6$)-alkyl, (C$_3$-C$_7$)cycloalkyl, (C cycloalkenyl, phenyl, substituted phenyl, phenylalkyl having 1 to 3 carbons in said alkyl, (substituted phenyl)alkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo-[2.2.1]heptan-2-yl, bicyclo[2.2.1]hept-5-en-2-yl or —(CH$_2$)$_n$—Q—R°; n is zero, 1 or 2; Q is a divalent radical derived from furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]-thiophene; R° is H or (C$_1$-C$_3$)alkyl; and R$^2$ is (C$_1$-C$_6$)alkyl, (C$_3$-C$_7$)cycloalkyl, benzyl, furyl, thienyl, pyridyl or

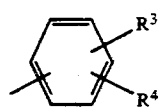

where R$^3$ and R$^4$ are each H, fluoro, chloro, (C$_1$C$_4$)-alkyl, (C$_1$C$_4$)alkoxy or trifluoromethyl.

That patent also discloses that said 2-oxinoole-1-carboxamides are inhibitors of cyclooxygenase and lipoxygenase, possess analgesic activity in mammals and are useful in treatment of pain and alleviation of symptoms of chronic diseases such as inflammation and pain associated with rheumatoid arthritis and osteoarthritis.

U.S. Pat. No. 4,556,672 discloses certain 3-acyl substituted-2-oxindole-1-carboxamides of the formula

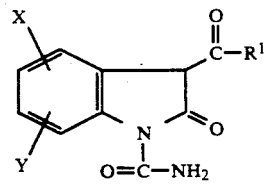

wherein X, Y and R$^1$ are as described above for the compounds of U.S. Pat. No. 4,569,942. The compounds of U.S. Pat. No. 4,556,672 are disclosed as having the same activity as the compounds of U.S. Pat. No. 4,569,942 discussed above.

U.S. Pat. No. 4,861,794 discloses the use of compounds of the formula

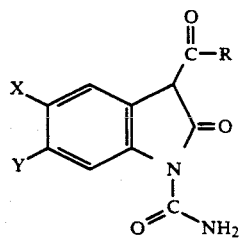

and the pharmaceutically-acceptable base salts thereof wherein X is H, Cl or F, Y is H or Cl and R is benzyl or thienyl to inhibit biosynthesis of interleukin-1 (IL-1) and to treat IL-1 mediated disorders and dysfunctions.

PCT patent application Ser. No. PCT/US88/03658, filed Oct. 18, 1988, describes non-steroidal antiinflammatory agents of the formula

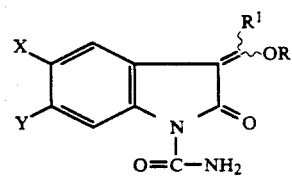

wherein each of X and Y is hydrogen, fluoro or chloro; R$^1$ is 2-thienyl or benzyl; and R is alkanoyl, cycloalkylcarbonyl, phenylalkanoyl, benzoyl and certain substituted benzoyl groups, thenoyl, omega-alkoxycarbonylalkanoyl, alkoxycarbonyl, phenoxycarbonyl, 1-alkoxycarbonyloxy, alkylsulfonyl, methylphenylsulfonyl and dialkyl phosphonate.

U.S. application Ser. No. 07/473,266, filed Jan. 31, 1990, which is a continuation-in-part of U.S. application Ser. No. 07/340,113, filed Apr. 18, 1989 and assigned to the assignee hereof, describes novel 3-substituted-2-oxindole compounds of the formula

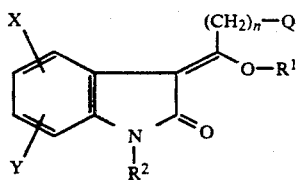
(I)

and the pharmaceutically-acceptable salts thereof, wherein

X is H, F, Cl, Br, $(C_1-C_6)$alkyl, $(C_3-C_8)$ )cyclo-alkyl, $NO_2$, $CF_3$, CN, SH, $S(O)_mR^3$, $OR^4$, $COR^4$ or $CONR^4R^5$;

Y is H, F, Cl, Br, $(C_1-C_6)$alkyl, $(C_3-C_8)$cyclo-alkyl, $NO_2$, $CF_3$, CN, SH, $S(O)_qR^{17}$, $OR^{18}$ or $CONR^{18}R^{19}$;

$R^1$ is H, alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omegaalkoxycarbonylalkanoyl, said alkoxy having one to three carbon atoms and said alkanoyl having three to five carbon atoms, alkoxy carbonyl of two to ten carbon atoms, phenoxycarbonyl, 1-(acyloxy)alkyl wherein acyl has one to four carbon atoms and said alkyl has two to four carbon atoms, 1-(alkoxycarbonyloxy)alkyl wherein said alkoxy has two to five carbon atoms and said alkyl has one to four carbon atoms, alkyl of one to three carbon atoms, alkylsulfonyl of one to three carbon atoms, methylphenylsulfonyl or dialkylphosphonate wherein each of said alkyl is one to three carbon atoms;

$R^2$ is $COR^6$, $CONR^7R^8$, $(C_1-C_6)$alkyl, $(C_3-C_8)$cycloalkyl, phenyl or mono- or disubstituted phenyl wherein the substituent or substituents are each Cl, F, Br, $(C_1-C_6)$alkyl, $(C_1-C_6)$alkoxy or $CF_3$;

Q is

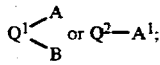

A is H, F, Cl, Br, I, $CF_3$, $OR^9$, $S(O_pR^{10}$, $COOR^{11}$, $CONR^9R^{11}$, CN, $NO_2$, $COR^{10}$, $CH_2OR^{11}$, $OCOR^{10}$, $NR^9R^{11}$, $N(R^9)COR^{11}$, $SO_2NR^9R^{11}$,

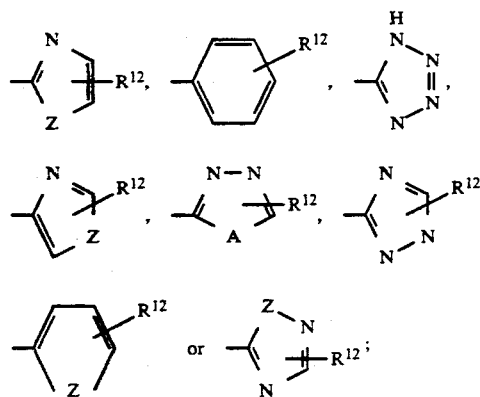

B is H, F, Cl, Br, I, $CF_3$, $OR^{13}$, $S(O)_tR^{14}$, $COOR^{15}$, $CONR^{13}R^{15}$, CN, $NO_2$, $COR^{14}$, $CH_2OR^{15}$, $OCOR^{14}$, $NR^{13}R^{15}$, $N(R^{13})COR^{15}$ or $SO_2NR^{13}R^{15}$;

provided that A and B cannot both be H; or A and B are taken together, bonded to the same ring carbon of $Q^1$ and equal oxo, or when A is not H, B is as defined above or $(C_1-C_4)$alkyl;

$A^1$ is F, Col, Br, I, $CF_3$, $OR^9$, $S(O)_pR^{10}$, $COOR^{11}$, $CONR^9R^{11}$, CN, $NO_2$, $COR^{10}$, $CH_2OR^{11}$, $OCOR^{10}$, $NR^9R^{11}$, $N(R^9)COR^{11}$ or $SO_2NR^9R^{11}$;

$Q^1$ is

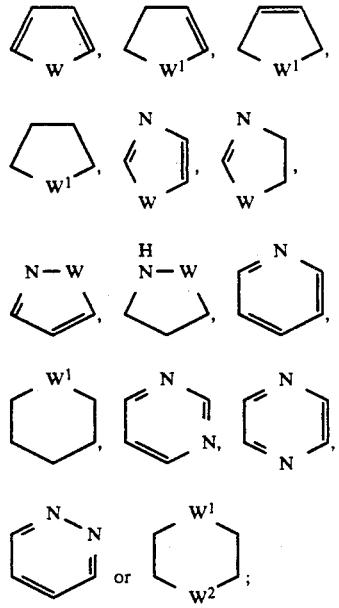

$Q^2$ is

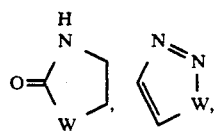

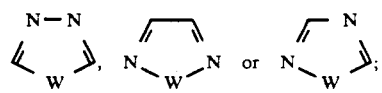

m, n, p, q and t are each zero, one or two;

W and Z are each O, S or $NR^{11}$;

$W^1$ and $W^2$ are each O, S or $NR^{10}$ provided that when one of $W^1$ or $W^2$ is O, S or $NR^{10}$, the other is O or S;

$R^3$, $R^6$, $R^{10}$, $R^{14}$ and $R^{17}$ are each $(C_1-C_6)$ alkyl or phenyl; $R^5$, $R^8$, $R^{11}$, $R^{15}$ and $R^{19}$ are each H, $(C_1-C_6)$ alkyl or phenyl; $R^4$, $R^7$, $R^9$, $R^{13}$ and $R^{18}$ are each H or $(C_1-C_6)$ alkyl; and $R^{12}$ is H, F, Cl, Br, $CF_3$ or $(C_1-C_6)$ alkyl. That application also describes inter alia a novel process which employs 1,1'-carbonyldiimidazole for preparing certain of the novel 3-substituted-2-oxindole compounds thereof.

Interleukin-1 (IL-1) has been reported to stimulate bone resorption both in vitro and in vivo. Hayward, M. and Fiedler-Nagy, Ch., Agents and Actions, 22, 251–254 (1987). It is also reported therein that IL-1, inter alia, induces the production of prostaglandin $E_2$ ($PGE_2$). $PGE_2$ is a stimulator of bone resorption and has been implicated in bone loss. See Hayward, M. A. and Caggiano, T. J., Annual Reports in Medicinal Chemistry, 22, Sect. IV, Chapter 17, 169–178 (1987). Osteoporosis is defined as a debilitory loss of bone mineral which results in higher fracture rates. See Hayward, M. A. and Caggiano, T. J., supra, and references cited therein.

Interleukin-1 has been reported to be involved in the pathogenesis of many diseases See Dinarello, C. A., J. Clin. Immunol., 5, 287–297 (1985), the teachings of which are incorporated herein by reference. Further still, elevated levels of IL-1 like material have been found to be associated with psoriasis. Camp, R. D., et al., J. Immunol., 137, 3469–3474 (1986).

DISCLOSURE OF THE INVENTION

The present invention provides novel 3-(1-substitutedpyrazoyl)-2-oxindole compounds of the formula

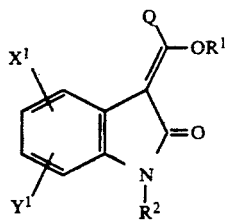

and the pharmaceutically-acceptable salts thereof, wherein

Q is 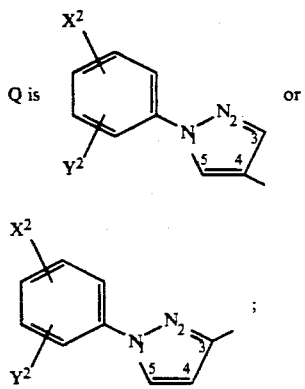

$X^1$ is H, F, Cl, Br, $(C_1-C_6)$alkyl, $NO_2$, $CF_3$, CN, $S(O)_m R^3$, $OR^4$, $COR^4$ or $CONR^4 R^5$;

$Y^1$ is H, F, Cl, Br, $(C_1-C_6)$alkyl, $NO_2$, $CF_3$, CN, $S(O)_n R^6$, $OR^7$ or $COR^7$, or $CONR^7 R^8$;

$X^2$ is H, F, Cl, Br, $(C_1C_4)$alkyl, $S(O)_p R^9$, $NO_2$, $COR^9$, $CONR^9 R^{10}$, CN or $CF_3$;

$Y^2$ is H, F, Cl, Br, $(C_1C_4)$alkyl, $S(O)_q R^{11}$, $NO_2$, $COR^{11}$, $CONR^{11} R^{12}$, CN or $CF_3$;

m and n are each zero, one or two; p and q are each one or two;

$R^1$ is H, alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl, said alkoxy having one to three carbon atoms and said alkanoyl having three to five carbon atoms, alkoxy carbonyl of two to ten carbon atoms, phenoxycarbonyl, 1-(acyloxy)alkyl wherein acyl has one to four carbon atoms and said alkyl has two to four carbon atoms, 1-(alkoxycarbonyloxy)alkyl wherein said alkoxy has two to five carbon atoms and said alkyl has one to four carbon atoms, alkyl of one to three carbon atoms, alkylsulfonyl of one to three carbon atoms, methylphenylsulfonyl or dialkylphosphonate wherein each of said alkyl is one to three carbon atoms;

$R^2$ is $COR^{13}$, $CONR^{14}R^{15}$, $(C_1-C_6)$alkyl;

$R^3$, $R^4$, $R^5$, $R^6$, $R^7$, $R^8$, $R^9$, $R^{10}$, $R^{11}$, $R^{12}$, $R^{14}$ and $R^{15}$ are each H or $(C_1-C_6)$alkyl, and $R^{13}$ is $(C_1-C_6)$alkyl.

While the compounds of formula I, above, are shown as enols, enol ethers and esters, it is to be understood that when $R^1$ is H the compounds of formula I can assume their tautomeric form of a ketone. That is,

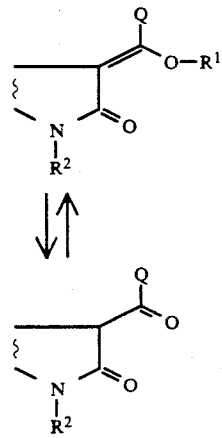

All such tautomeric forms are within the scope of this invention and the appendant claims, and are deemed to be depicted by formula I. Further, the substituents on the exocyclic double bond at the 3-position of the compounds for formula I can be syn, anti or a mixture of both. Thus, the compounds of formula I having the structures

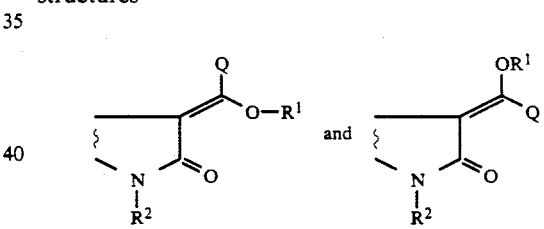

and mixtures thereof are within the scope of this invention and all such isomers are deemed to be depicted by formula I and within the scope of the appendant claims.

The compounds of formula I wherein $R^1$ is other than H are prodrugs of the compounds of formula I wherein $R^1$ is H and the salts thereof.

The term "prodrug" refers to compounds which are drug precursors which, following administration to and absorption by a mammal, release the drug in vivo via some metabolic process.

After gastrointestinal absorption, the prodrugs are hydrolyzed in vivo to the corresponding compounds of formula I where R is H, or a salt thereof. Since the prodrugs of the invention are not enolic acids, exposure of the gastrointestinal tract to the acidic parent compound is thereby minimized.

A preferred group of compounds of this invention is those of formula I, above, wherein $R^1$ is H. Another preferred group of compounds is those of formula I wherein $R^2$ is $CONR^{14}R^{15}$ and $R^2$ is where $CONR^{14}R^{15}$ where $R^{14}$ and $R^{15}$ are each H. Yet another preferred group of compounds is those of formula I wherein Q is

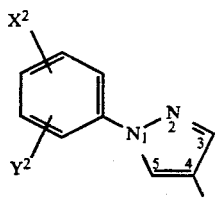

Particularly preferred are those compounds of formula I wherein $R^1$ is H, $R^2$ is $CONR^{14}R^{15}$ where $R^{14}$ and $R^{15}$ are each H, $X^1$ is H, F, Cl or $CF_3$, $Y^1$ is H or Cl and Q is

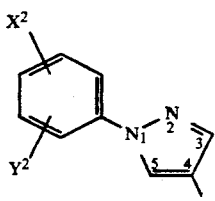

where $X^2$ is H or F and $Y^2$ is H or F. Also particularly preferred are the above preferred compounds wherein $X^1$ and $Y^1$ are substitutions at positions 5, 6 or 7 with positions 5 and 6 being even more preferred still.

The compounds of formula I, above, wherein $R^1$ is H are active as inhibitors of prostaglandin $H_2$ synthase (cyclooxygenase), as inhibitors of 5-lipoxygenase and as inhibitors of interleukin-1 (IL-1) biosynthesis in a mammal. Thus, the compounds of formula I are useful for inhibition of prostaglandin $H_2$ synthase and IL-1 biosynthesis in a mammal. The compounds of formula I, in addition to their usefulness as such inhibitors, per se, are useful as analgesic, antiinflammatory and antiarthritic agents in the treatment of chronic inflammatory diseases in mammals.

The present invention also provides pharmaceutical compositions comprising compounds of formula I. Further, methods of inhibiting prostaglandin $H_2$ synthase and biosynthesis of interleukin-1 in a mammal by administering an effective amount of a compound of formula I to said mammal are provided by this invention. Also provided by the present invention are methods of treating interleukin-1 mediated disorders and immune dysfunctions and/or chronic inflammatory diseases in mammal by administering to said mammal an effective amount of a compound of formula I. Such chronic inflammatory diseases within the scope of this invention include, but are not limited to, psoriasis, rheumatoid arthritis and osteoarthritis.

Further, still, the invention provides novel esters of the formulae

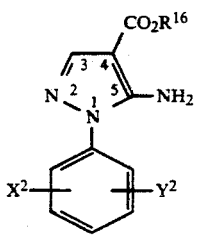

and the acid addition salts thereof, wherein $X^2$ is H, F, Cl, Br, $(C_1-C_4)$alkyl, $S(O)_pR^9$, $NO_2$, $COR^9$, $CONR^9R^{10}$, CN or $CF_3$;

$Y^2$ is H, F, Cl, Br, $(C_1-C_4)$alkyl, $S(O)_qR^{11}$, $NO_2$, $COR^{11}$, $CONR^{11}R^{12}$, CN or $CF_3$;

p and q are each one or two;

$R^9$, $R^{10}$, $R^{11}$ and $R^{12}$ are each H or $(C_1-C_6)$alkyl; and $R^{16}$ is $(C_1-C_4)$alkyl, provided that when one of $X^2$ and $Y^2$ is H, the other is not H, Cl, $NO_2$, $CF_3$ or $CH_3$.

The compounds of formula II, above, are useful as intermediates in the preparation of the 3-(1-substituted-pyrazoyl)-2-oxindole compounds of formula I, above.

Yet further still, this invention provides novel carboxylic acids and esters of the formulae

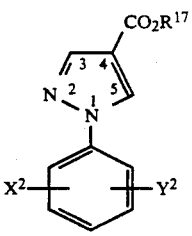

and the salts thereof, wherein $X^2$ is H, F, Cl, Br, $(C_1-C_4)$alkyl, $S(O)_pR^9$, $NO_2$, $COR^9$, $CONR^9$, $R^{10}$, CN or $CF_3$;

$Y^2$ is H, F, Cl, Br, $(C_1C_4)$alkyl, $S(O)_qR^{11}$, $NO_2$, $COR^{11}$, $CONR^{11}R^{12}$, CN or $CF_3$;

p and q are each one or two;

$R^9$, $R^{10}$, $R^{11}$ and $R^{12}$ are each H or $(C_1-C_6)$alkyl; and $R^{17}$ is H or $(C_1C_4)$alkyl, provided that when one of $X^2$ and $Y^2$ is H, the other is not H, F, Cl, Br, $(C_1C_4)$alkyl, $NO_2$ or $CF_3$.

This invention further provides novel compounds of the formula

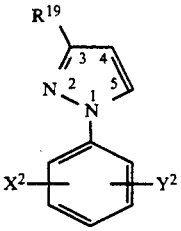

and the salts thereof, wherein $X^2$ is H, F, Cl, Br, $(C_1-C_4)$alkyl, $S(O)_pR^9$, $NO_2$, $COR^9$, $CONR^9$, $R^{10}$, CN or $CF_3$;

$Y^2$ is H, F, Cl, Br, $(C_1C_4)$alkyl, $S(O)_qR^{11}$, $NO_2$, $COR^{11}$, $CONR^{11}R^{12}$, CN or $CF_3$;

p and q are each one or two;

$R^9$, $R^{10}$, $R^{11}$ and $R^{12}$ are each H or $(C_1-C_6)$alkyl;

$R^{19}$ is $CH_3$ or $CO_2R^{17}$; and $R^{17}$ is H or $(C_1-C_4)$alkyl; provided that when $R^{19}$ is $CO_2R^{17}$ and one of $X^2$ and $Y^2$ is H, the other is not Cl, Br, $CH_3$ or $NO_2$.

The compounds of formulae IV and V, above, are useful as intermediates in the preparation of the 3-(1-substituted-pyrazoyl)-2-oxindole compounds of formula I, above. This invention also provides a novel process for producing certain of the 3-(1-substituted-pyrazoyl)-2-oxindole compounds of formula I, above, wherein $R^1$ is H and $R^2$ is $R^{18}$ as defined below. The novel process comprises reacting a compound of the formula $$Q-COOH \qquad (VI)$$

where Z is as defined above for compounds of formula I, with a molar excess of 1,1'-carbonyldiimidazole in a reaction inert solvent under an inert atmosphere and reacting the product thereof in the presence of a basic agent with a 2-oxindole derivative of the formula

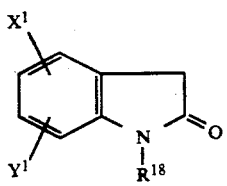

(VIII')

wherein $X^1$ and $Y^1$ are as defined above for compounds of formula I and $R^{18}$ is $COR^{13}$ or $CONR^{14}R^{15}$ where $R^{13}$, $R^{14}$, $R^{15}$ are as defined above for compounds of formula I, at about 0°–50° C., in a reaction inert solvent under an inert atmosphere.

DETAILED DESCRIPTION

REACTION SCHEME A

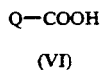

Q—COOH (VI)

↓

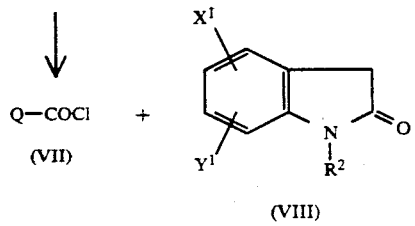

↓

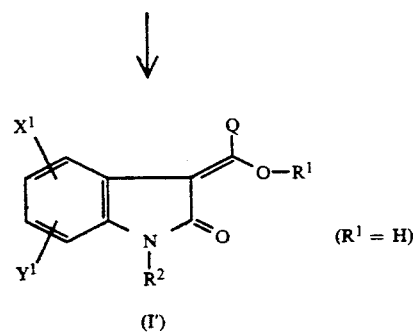

A method for preparation of compounds of formula I wherein $R^1$ is H is shown in Reaction Scheme A, above, and is described as follows. The substituted 2-oxindole compounds of formula VIII are prepared according to the methods disclosed in U.S. Pat. Nos. 3,634,453, 4,566,672, 4,569,942, 4,695,571, EP 175551 and the references cited therein. The teachings thereof are incorporated herein by reference. The carboxylic acid compounds of formula VII are prepared as described below and are activated by reacting the compound of formula VI with a molar excess of thionyl chloride, optionally in the presence of a reaction inert solvent. Appropriate reaction inert solvents are those which will at least partially dissolve one or all of the reactants and will not adversely interact with either the reactants or the product. The resulting carbonyl chloride compound of formula VII is dissolved in a reaction inert solvent and slowly added to a solution, cooled to about 0° C., comprising approximately an equimolar amount of the substituted 2-oxindole of formula VIII and a molar excess of a basic agent in a reaction inert solvent. The reaction inert solvent is as described above but, in practice, a polar aprotic solvent, such as N,N-dimethylformamide, N,N-dimethylacetamide, N-methylpyrrolidone, or dimethyl sulfoxide, is commonly used. A preferred solvent is N,N-dimethylformamide. A wide variety of basic agents can be used in the reaction between a carbonyl chloride compound of formula VII and a substituted 2-oxindole compound of formula VIII. However, preferred basic agents are tertiary amines, such as trimethylamine, triethylamine, tributylamine, N-methylmorpholine, N-methylpiperidine, pyridine and 4-(N,N-dimethylamino)pyridine, with a particularly preferred basic agent being 4-(N,N-dimethylamino)pyridine. Following addition of the carbonyl chloride compound of formula VII to the substituted 2-oxindole compound of formula VIII, the reaction is permitted to warm to about 25° C. and permitted to continue at that temperature. Reaction times of about 30 minutes to two hours are common. At the end of the reaction, the reaction mixture is acidified and then the product is recovered such as by filtration. The product can then be washed, dried and further purified by standard methods such as recrystallization.

REACTION SCHEME B

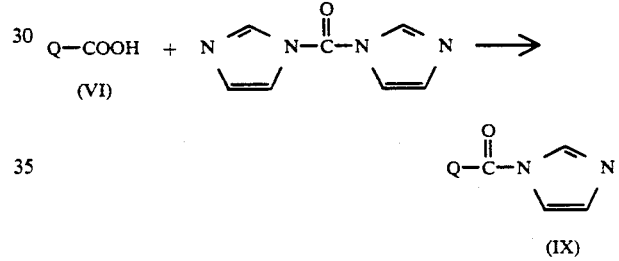

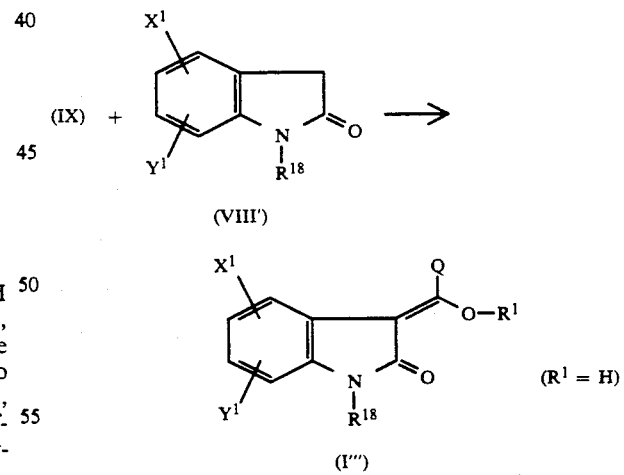

Alternatively, the compounds of formula I wherein $R^1$ is H can be prepared by the novel process of this invention shown in Reaction Scheme B, above, and described below. A carboxylic acid compound of formula VI, prepared as described below, is reacted with a slight molar excess of 1,1'-carbonyldiimidazole in a reaction inert solvent. The reaction is carried out at about 25° C. and is stirred under an inert atmosphere. The reaction is permitted to proceed for about two hours whereupon the entire reaction mixture is added to a mixture comprising an approximately equimolar amount of a substituted 2-oxindole compound of formula VIII', prepared as described above, in the presence of a molar excess of a basic agent in a reaction inert solvent under an inert atmosphere. Appropriate reaction inert solvents are those as described above for Reaction Scheme A and a preferred solvent for use herein is N,N-dimethylformamide. An inert atmosphere is obtained by carrying the reaction out under an inert gas such as nitrogen or argon. Appropriate basic agents are those as described above for Reaction Scheme A and preferred basic agents are 4-(N,N-dimethylamino)pyridine and triethylamine.

Another method useful for preparation of compounds of formula I wherein $R^1$ is H comprises the attachment of the

substituent to the 3-position of the requisite 2-oxindole compound of the formula

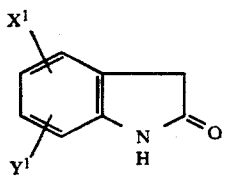

(X)

by reacting a compound of the formula X with a derivative of the appropriate acid of formula VI, above, according to the methods described in U.S. Pat. No. 4,556,672. The resulting compounds of the formula

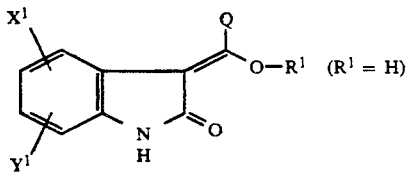

(XI)

are then converted to the corresponding compounds of formula I', above, according to the methods described in U.S. Pat. Nos. 3,634,453; 4,556,672; 4,569,942; 4,695,571; EP 175551 and the references cited therein.

REACTION SCHEME C

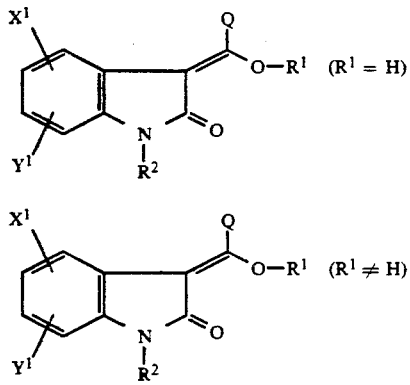

There are tow methods which can be employed in the synthesis of compounds of formula I wherein $R^1$ is other than hydrogen (formula I" in Reaction Scheme C). The first method comprises treating a solution of the appropriate substituted-2-oxindole of formula I', above, and an equimolar amount of triethylamine in a reaction-inert solvent such as chloroform, at 0° C. with an equimolar amount, plus a slight excess of the requisite acid chloride, chloroformate, oxonium salt or alkylating agents. After 2 hours, the reaction is allowed to warm to room temperature and remain for about 2-3 hours. If the starting oxindole is not completely reacted the mixture is cooled to 0° C., additional acylating or alkylating agent is added and the process repeated until all the starting oxindole is consumed.

The product is isolated from the reaction solvent by filtration and washed with 1N hydrochloric acid followed by partitioning in an organic solvent and a saturated sodium bicarbonate solution. The organic layer is dried, filtered and concentrated in vacuo. The resulting product is purified by recrystallization or chromatography.

The second procedure, useful in the preparation of the compounds of the present invention wherein $R^1$ is not hydrogen, consists of contacting, in an anhydrous reaction-inert solvent such as acetone, the appropriate substituted-2-oxindole of formula I', a three-fold molar excess of the requisite alpha-chloroalkylcarbonate, a five-fold molar excess of sodium iodide and a two-fold molar excess of anhydrous potassium carbonate (dried under high vacuum at 165° C. for 1 hour) and heating said reaction mixture at reflux for 16 hours.

The reaction mixture is cooled, diluted with water and the product extracted with a water-immiscible solvent, such as diethyl ether or chloroform. The combined extracts are dried, filtered and the filtrate concentrated in vacuo. The resulting crude product is purified by recrystallization and/or chromatography.

Certain of the carboxylic acid compounds of formula II are known and the carboxylic acid compounds of formula VI including the novel compounds of formulae IV and V are prepared according to known methods, or methods analogous to known methods. Such methods may include the preparation of the corresponding esters of the respective carboxylic acids in which cases hydrolysis by known procedures yields the carboxylic acid of interest. For such methods, consult: U.S. Pat. No. 4,220,792, Beck, J. R., et al., J. Heterocyclic Chem. 24: 267–270 (1987), von L. Claisen, et al., Annalen der Chemie 278: 274 (1894) and H. El Khadem, et al., J. Chem. Soc. (C), 1845–1848 (1968) the teachings of which are incorporated herein by reference.

The compounds of the formula I wherein $R^1$ is H are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Typical salts of the compounds of formula I which can be prepared are primary, secondary and tertiary amine salts, alkali metal salts and alkaline earth metal salts. Especially valuable are the ethanolamine, diethanolamine and triethanolamine salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary glucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

The ability of the compounds of formula I to inhibit interleukin-1 biosynthesis is demonstrated by the assay procedure described below.

C3H/HeN mice (Charles River, Wilmington, Mass.) are sacrificed by cervical dislocation and their abdomens sprayed with 70% ethanol to prevent bacterial contamination of the subsequent cellular preparation. Into the peritoneum of each mouse is injected 8 ml of RPMI[1], containing a 5% FCS[2], penicillin-streptomycin (100 units/ml - 100 ug/ml) and glutamine (2mM). The peritoneum is kneaded to help free cells. Then, an incision through the skin of the abdomen is made to expose the underlying muscle layer. The peritoneal fluid is removed with a 20 gauge needle by inserting the needle, bevel down, through the exposed muscle layer just below the sternum. The peritoneal fluid from six mice is pooled in a plastic conical tube and microscopically examined for bacterial contamination. Uncontaminated fluid is centrifuged at about 600xg for six minutes and the supernatant decanted. The pelleted cells from five to six tubes are combined and resuspended in a total of 20 ml of RPMI-FCS[3]. The cell number is then ascertained using a hemacytometer and cell viability determined with Trypan Blue staining also using a hemacytometer. The cells are then diluted to $3 \times 10^6$ cells/ml using RPMI-FCS. To the wells of a 35 mm well plate is added 1 ml of the above cell suspension. The cells are incubated for 2 hours at 37° C. in a 5% $CO_2$ atmosphere to cause adherence of the macrophages to the walls of the wells. The supernatant is removed by swirling the wells vigorously and decanting. The adherent cells (i.e., macrophages) are washed twice with RPMI-SF[4]. To the wells containing adherent cells is added 1 ml of the compound under study at concentrations ranging from 0.1 to 100 ug/ml in RPMI-SF or 1 ml of RPMI-SF as a control. Then, 100 ul of LPS[5] in RPMI-SF (1 mg/5 ml) is added to each well. The plates are incubated at 37° C. in a 5% $CO_2$ atmosphere for 24 hours. The supernatants are removed and either assayed for IL-1 immediately or otherwise refrigerated or frozen for subsequent assay.

[1]RPMI-1640 medium (Hazelton Research Products, Inc., Lenexa, Kans.)
[2]Fetal calf serum which has been screened for good responsiveness to IL-1 in the thymocyte assay (Hyclone Laboratories, Logan, Utah) and for low spontaneous proliferation in the absence of IL-1.
[3]RPMI-1640 medium containing 5% fetal calf serum
[4]RPMI containing penicillin-streptomycin (100 units/ml-100 ug/ml) and glutamine (2 mM).
[5]Refined purified lipopolysaccharide from *Salmonella minnesota* which has been checked to determine that the C3H/HeJ mouse in unresponsive thereto.

The supernatants are assayed quantitatively for IL-1 according to the receptor binding assay described below. A standard curve is generated as follows. EL4-6.1 murine thymoma cells [$10-15 \times 10^6$ cells in 0.4 ml binding buffer (RPMI 1640, 5% FCS, 25 mM HEPES, 0.01% NaN3, pH 7.3)] are added to varying amounts of unlabeled murine rIL-1α [recombinant IL-1α produced in *Escherichia coli* from the published sequence of amino acids 115-270 for IL-1α, Lomedico, P. M., et al., Nature, 312, 458-462 (1984)] (40 pg to 40 ng in 0.5 ml buffer) and incubated for 1 hour at 4° C. with continuous shaking, after which 0.8 ng (0.1 ml) of human $^{125}$I-rIL-1β (New England Nuclear, Boston, Mass.) is added and shaking continued for an additional 3 hours. Samples are filtered with a Yeda apparatus (Linca Co., Tel-Aviv, Israel) through Whatman GF/C2.4 cm glass fiber filters (blocked with 0.5% powdered milk for 2 hours at 37° C.) and washed once with 3 ml of ice-cold buffer. Filters are counted in a Searle gamma counter and nonspecific binding is taken as the cpm bound in the presence of 200 ng unlabeled rIL-1α. A Hill calibration curve is constructed by plotting log (Y/100-Y) vs. log C where Y represents the percent of control $^{125}$I-rIL-1β binding and C is the concentration of unlabeled rIL-1α. A linear least-squares line is fitted through Y values between 20 to 80%. Then, to quantitate IL-1 levels in the supernatants obtained as described above, diluted supernatants replace rIL-1α in the above protocol and measured percent binding values are used to determine i0 IL-1 concentrations from a standard Hill plot. Each dilution is assayed in duplicate and generally only dilutions with Y values between 20 to 80% are used to calculate average IL-1 levels.

The ability of the compounds of formula I to inhibit prostaglandin $H_2$ synthase and 5-lipoxygenase is demonstrated by the following assay procedure. By employing the procedure described below the levels of known products of prostaglandin $H_2$ synthase and 5-lipoxygenase are measured for cells treated with the compound under study with inhibition of prostaglandin $H_2$ synthase and/or 5-lipoxygenase being evidenced by a decrease in the amount of, or absence of, the known products of those enzymes.

RBL-1 cells, maintained in monolayer, are grown for 1 to 2 days in Spinner culture in Minimum Essential Medium (Eagle) with Earle's Salts plus 15% fetal bovine serum supplemented with antibiotic/antimycotic solution (Gibco) according to the method of Jakschik, B. A., et al., Nature 287:51-52 (1980). The cells are washed twice and resuspended in cold RPMI 1640 to a cell density of $4 \times 10^6$ cells/ml. Then, a 0.25 ml aliquot of the compound under study at the desired concentration in RPMI 1640 is equilibrated at 37° C. for 5 minutes. To the equilibrated aliquot is added a 0.25 ml aliquot of prewarmed cell suspension and the mixture is incubated at 37° C. for 5 minutes. A 10 ul solution containing $^{14}$C-arachidonic acid and A-23187 (calcium ionophore, Sigma Chemical) is added and the mixture is incubated at 37° C. for another 5 minutes. Then, 267 ul of acetonitrile/0.3% acetic acid is added and the mixture is allowed to stand on ice for 30 minutes. The tube containing the mixture is vortexed, clarified by centrifugation (3000 rpm, 10 minutes) and the supernatant is decanted and re-centrifuged for 2 minutes in a microfuge at high speed. A 100 ul aliquot of the supernatant then is analyzed by HPLC on a Perkin Elmer-HS (3 micron) column using a gradient solvent system of acetonitrile/$H_2O$ with 0.1% trifluoroacetic acid and a flow rate of 2 ml/min. Radioactivity detection is accomplished with a Berthold LB504 Radioactivity Monitor equipped with an 800 ul flow cell mixing 2.4 ml/min of Omnifluor (Trademark of New England Nuclear, Boston, Mass.) with the column effluent. Quantitation of the eluted radioactivity is carried out by the use of a Spectra Physics SP4200 computing integrator. The data so obtained is used in a data-reduction program where the integration units for each product are calculated as percent of the total integration units and compared to average control levels.

The compounds of formula I possess analgesic activity. This activity is demonstrated in mice by showing blockage of the abdominal stretching induced by administration of 2-phenyl-1,4-benzoquinone (PBQ). The method used is based on that of Siegmund et al., Proc. Soc. Exp. Biol. Med., 95, 729–731, (1957), as adapted for high throughput (see further Milne and Twomey, Agents and Actions, 10, 31–37, [1980]). All mice were fasted overnight prior to drug administration and testing.

The compounds of formula I are dissolved or suspended in a vehicle consisting of ethanol (5%), emulphor 620 (a mixture of polyoxyethylene fatty acid esters, 5%) and saline (90%). This vehicle also serves as control. Doses were on a logarithmic scale (i.e., ... 0.32, 1.0, 3.2, 10, 32 ... mg/kg). The route of administration is oral, with concentrations varied to allow a constant dosage volume of 10 ml/kg of body weight. The aforesaid method of Milne and Twomey is used to determine efficacy and potency. Mice are treated with compounds orally, and one hour later received PBQ, 2 mg/kg, intraperitoneally. Individual mice are then immediately placed in a warmed lucite chamber, and, starting five minutes after PBQ administration, the number of abdominal constrictions during the subsequent 5 minutes is recorded. The degree of analgesic protection (% MPE) is calculated on the basis of suppression of abdominal constriction relative to counts from concurrent control animals run on the same day. At least four such determinations (N=5) provide dose-response data for generation of an $MPE_{50}$, the best estimate of the dose that reduces abdominal constriction to 50% of control levels.

The compounds of formula I also possess antiinflammatory activity. This activity is demonstrated in rats by a method based on the standard carrageenin induced rat foot edema test (Winter et al., Proc. Soc. Exp. Biol. Med., 111, 544 [1963]).

Unanesthetized, adult, male, albino rats of 150 g to 190 g body weight are numbered, weighed, and an ink mark placed on the right lateral malleolus. Each paw is immersed in mercury exactly to the ink mark. The mercury is contained in a glass cylinder, connected to a Statham Pressure Transducer. The output from the transducer is fed through a control unit to a microvoltameter. The volume of mercury displaced by the immersed paw is read. Drugs are given by gavage. One hour after drug administration, edema is induced by injection of 0.05 ml of 1% solution of carrageenin into the plantar tissue of the marked paws. Immediately thereafter, the volume of the injected foot is measured. The increase in foot volume 3 hours after the injection of carrageenin constitutes the individual inflammatory response.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

The ability of the compounds of formula I to inhibit IL-1 biosynthesis makes them useful as IL-1 biosynthesis inhibitors, per se. It also makes them useful in treating IL-1 mediated disorders and immune dysfunctions in a mammal. Said IL-1 mediated disorders include, but are not limited to bone and connective tissue metabolism disorders such as osteoporosis, periodontal disease and tissue scarring. IL-1 mediated immune dysfunctions include, but are not limited to, allergy and psoriasis.

The ability of the compounds of formula I to inhibit prostaglandin $H_2$ synthase makes them useful as prostaglandin $H_2$ synthase inhibitors, per se, as the functioning of that enzyme is known to be involved with the pathogenesis of arthritic joints in mammals.

When a compound of formula I or a pharmaceutically-acceptable salt thereof is to be used as an inhibitor of IL-1, an inhibitor of prostaglandin $H_2$ synthase, an analgesic agent or an antiinflammatory agent, it can be administered to a mammalian subject either alone, or, preferably, in combination with pharmaceutically-acceptable carriers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be about 5 mg to 500 mg as needed (e.g., every four to twenty-four hours). For chronic administration to alleviate (treat) inflammation and pain, inhibit Il-1 biosynthesis and/or inhibit prostaglandin H2 synthase in most instances an effective dose will be from about 5 mg to 1.0 g per day, and preferably 50 mg to 500 mg per day, in single or divided doses. On the other hand, it may be necessary to use dosages outside these limits in some cases.

The following Examples are illustrative of this invention and are not to be construed as limited in any way the scope hereof.

EXAMPLE 1

5-Chloro-3-[4-(1-phenylpyrazoyl)]2-oxindole-1-carboxamide

A 1.25 g (6.64 mmole) sample of 1-phenyl-4-pyrazolecarboxylic acid (prepared by basic cleavage of the corresponding ethyl ester: Beck, J., et al., J. Heterocyclic Chem. 24, 267 (1987)) was combined with 1.17 g (7.20 mmole) of 1,1'-carbonyldiimidazole in 10 ml of N,N-dimethylformamide and stirred at room temperature under argon. After two hours the reaction contents were transferred to an addition funnel and added dropwise to a mixture of 1.17 g (5.54 mmole) of 5-chloro-2-oxindole-1-carboxamide and 1.83 g (14.95 mmole) of 4-(N,N-dimethylamino)pyridine in 45 ml of N,N-dimethylformamide at room temperature under an inert atmosphere. The reaction mixture was stirred for three hours and then poured into 85 ml of 0.35 N hydrochloric acid to precipitate 650 mg of crude greenish-yellow product. Recrystallization from glacial acetic acid gave the pure title compound, 230 mg (0.60 mmole, 11% yield) as a yellow solid, m.p. 253-4° C.

Analysis: Calculated for $C_{19}H_{13}C^1N_4O_3$: C, 59.93; H, 3.44; N, 14.71%. Found: C, 59.83; H, 3.44; N, 4.46%.

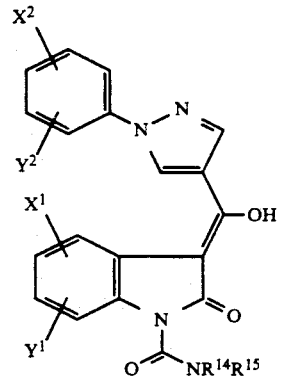

| Ex. No. | $R^{14}$ | $R^{15}$ | $X^1$ | $Y^1$ | $X^2$ | $Y^2$ | m.p. (°C.) | Analysis |
|---|---|---|---|---|---|---|---|---|
| 2 | H | CH2CH3 | H | 6-Cl | H | H | 215-17 (acetic acid) | Calc'd For: $C_{21}H_{17}ClN_4O_3$: C, 61.69; H, 4.19; N, 13.70% Found: C, 61.06; H, 4.01, N, 13.46% |
| 3 | H | H | 5-F | 6-Cl | H | H | 253-55 (acetic acid) | Calc'd For: $C_{19}H_{12}ClFN_4O_3$: C, 57.22; H, 3.03; N, 14.05% Found: C, 56.82; H, 2.87; N, 13.79% |

EXAMPLE 4

5-Chloro-3-[4-(1-(4-chlorophenyl)pyrazoyl)]-2-oxindole-1-carboxamide

A 1.00 g (4.49 mmole) sample of 1-(4-chlorophenyl)-4-pyrazolecarboxylic acid (prepared as described in Preparation N) was suspended in 20 ml of thionyl chloride and warmed to reflux. After heating for 1 hour, excess thionyl chloride was evaporated to give the crude acid chloride as an off-white solid. This acid chloride was dissolved in 5 ml of N,N-dimethylformamide and added slowly dropwise to a 30 ml solution of 857 mg (4.07 mmole) of 5-chloro-2-oxindole-1-carboxamide and 1.34 g (10.98 mmole) of 4-(N,N-dimethylamino)pyridine. After stirring at room temperature for forty-five minutes, the reaction was poured into 60 ml of 0.5 N hydrochloric acid and filtered to give the crude product. Trituration with 40 ml of hot glacial acetic acid furnished the pure title compound (1.26 g, 75% yield) as a light yellow solid, m.p. 255-7° C.

Analysis: Calculated for $C_{19}H_{12}Cl_2N_4O_3$: C, 54.96; H, 2.91; N, 13.49%. Found: C, 54.87; H, 2.71; N, 13.36%.

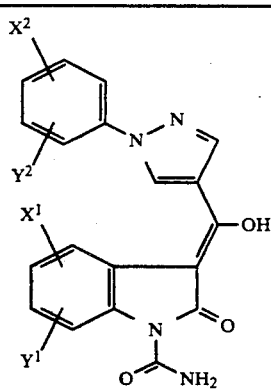

| Ex. No. | $X^1$ | $Y^1$ | $X^2$ | $Y^2$ | m.p. (°C.) | Analysis |
|---|---|---|---|---|---|---|
| 5 | 5-Cl | H | H | 4-OCH$_3$ | 246–48 (acetic acid) | Calc'd For: $C_{20}H_{15}ClN_4O_4$: C, 58.47; H, 3.68; N, 13.64% Found: C, 58.45; H, 3.36; N, 13.59% |
| 6 | H | 6-Cl | H | H | 259–60 (acetic acid) | Calc'd For: $C_{19}H_{13}ClN_4O_3$: C, 59.93; H, 3.44; N, 14.71% Found: C, 59.83; H, 3.27; N, 14.83% |
| 7 | 5-CF$_3$ | H | H | H | 242–45 (acetic acid) | Calc'd For: $C_{20}H_{13}F_3N_4O_3$: C, 57.97; H, 3.16; N, 13.52% Found: C, 57.94; H, 2.91; N, 13.42% |
| 8 | 5-Cl | H | H | 4-F | 254–56 (acetic acid) | Calc'd For: $C_{19}H_{12}ClFN_4O_3$: C, 57.22; H, 3.03; N, 14.05% Found: C, 57.32; H, 2.89; N, 14.02% |
| 9 | 5-Cl | H | H | 3-F | 262–64 (acetic acid) | Calc'd For: $C_{19}H_{12}ClFN_4O_3$: C, 57.22; H, 3.03; N, 14.05% Found: C, 57.28; H, 2.98; N, 14.00% |
| 10 | 5-Cl | H | 2-F | 4-F | 262–64 (acetic acid) | Calc'd For: $C_{19}H_{11}ClF_2N_4O_3$: C, 54.75; H, 2.66; N, 13.44% Found: C, 55.08; H, 2.65; N, 13.28% |
| 11 | 5-Cl | H | 2-F | 5-F | 276–78 (acetic acid) | Calc'd For: $C_{19}H_{11}ClF_2N_4O_3$: C, 54.75; H, 2.66; N, 13.44% Found: C, 55.68; H, 2.35; N, 13.38% |
| 12 | 5-Cl | H | H | 4-Br | 270–72 (acetic acid) | Calc'd For: $C_{19}H_{12}BrClN_4O_3$: C, 49.64; H, 2.63; N, 12.19% Found: C, 49.73; H, 2.54; N, 11.97% |
| 13 | 5-Cl | H | 3-Cl | 4-Cl | 267–69 (acetic acid) | Calc'd For: $C_{19}H_{11}Cl_3N_4O_3$: C, 50.74; H, 2.47; N, 12.46% Found: C, 50.81; H, 2.41; N, 12.37% |
| 14 | 5-Cl | H | H | 3-CF$_3$ | 240–2 (acetic acid) | Calc'd For: $C_{20}H_{12}ClF_3N_4O_3$: C, 53.52; H, 2.70; N, 12.48% Found: C, 53.60; H, 2.47; N, 12.39% |

PREPARATION A

Ethyl-5-Amino-1-(4-fluorophenyl)-1H-pyrazole-4-carboxylate

A stirred mixture of 11.38 g (70.0 mmole) of a commercially available sample of 4-fluorophenylhydrazine hydrochloride, 11.84 g (70.0 mmole) of ethyl (ethoxymethylene)cyanoacetate and 9.67 g (70.0 mmole) of potassium carbonate in 100 ml of ethanol was refluxed overnight and then treated with 300 ml of water. The precipitate was filtered and dried in vacuo to furnish 12.87 g (74% yield) of pale yellow crystalline solid. The sample was recrystallized from ethanol m.p. 151-2° C.

Analysis: Calculated for $C_{12}H_{12}FN_3O_2$: C, 57.82; H, 4.85; N, 16.86%. Found: C, 57.82; H, 4.78; N, 16.79%.

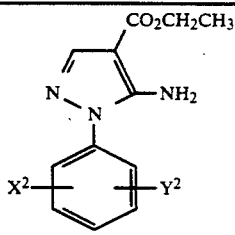

| PREPARATION | $X^2$ | $Y^2$ | m.p. (°C.) | Analysis |
|---|---|---|---|---|
| B | 2-F | 5-F | 84–6 (isopropyl) | Calc'd For: $C_{12}H_{11}F_2N_3O_2$: C, 53.93; H, 4.15; N, 15.72% |

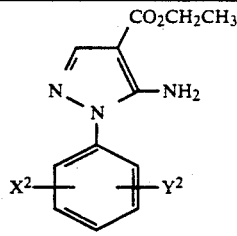

| PREP-ARA-TION | $X^2$ | $Y^2$ | m.p. (°C.) | Analysis |
|---|---|---|---|---|
| | | | ether) | Found: C, 53.81; H, 4.07; N, 15.64% |
| C | H | 3-F | 119–21 (ethanol) | Calc'd For: $C_{12}H_{12}FN_3O_2$: C, 57.82; H, 4.85; N, 16.86% Found: C, 57.69; H, 4.95; N, 16.87% |
| D | H | 4-Br | 130–32 (ethanol) | Calc'd For: $C_{12}H_{12}BrN_3O_2$: C, 46.47; H, 3.90; N, 13.55% Found: C, 46.53; H, 3.76; N, 13.46% |
| E | 2-F | 4-F | 131–33 (ethanol) | Calc'd For: $C_{12}H_{11}F_2N_3O_2$: C, 53.93; H, 4.15; N, 15.72% Found: C, 53.87; H, 4.03; N, 15.69% |

PREPARATION G

Ethyl 1-(4-fluorophenyl)-1H-pyrazole-4-carboxylate

A stirred suspension of ethyl 5-amino-1-(4-fluorophenyl)-1H-pyrazole-4-carboxylate (7.48 g, 30.0 mmole), prepared as described in Preparation A, above, and isopentyl nitrite (7.03 g, 60.0 mmole) in 80 ml of tetrahydrofuran was refluxed for twenty-four hours and then evaporated in vacuo. The residue was triturated with 50 ml of methanol and filtered to furnish 5.18 g (74% yield) of off-white solid. The sample was recrystallized from ethanol, m.p. 119–21° C.

Analysis: Calculated for $C_{12}H_{11}FN_2O_2$: C, 61.53; H, 4.73; N, 11.96%. Found: C, 61.41; H, 4.51; N, 11.95%.

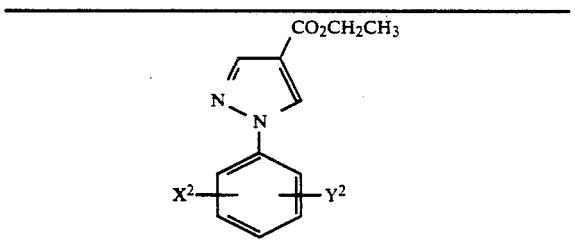

| PREP-ARA-TION | $X^2$ | $Y^2$ | m.p. (°C.) | Analysis |
|---|---|---|---|---|
| H | 2-F | 5-F | 77–9 (methanol) | Calc'd For: $C_{12}H_{10}F_2N_2O_2$: C, 57.14; H, 4.00; N, 11.11% Found: C, 57.04; H, 4.01; N, 11.09% |
| I | H | 3-F | 115–17 (methanol) | Calc'd For: $C_{12}H_{11}FN_2O_2$: C, 61.53; H, 4.73; N, 11.96% Found: C, 61.52; H, 4.43; N, 11.81% |
| J | H | 4-Br | 129–31 (ethanol) | Calc'd For: $C_{12}H_{11}BrN_2O_2$: C, 48.83; H, 3.76; N, 9.49% Found: C, 48.81; H, 3.52; N, 9.41% |
| K | 2-F | 4-F | 66–8 (methanol) | Calc'd For: $C_{12}H_{10}F_2N_2O_2$: C, 57.14; H, 4.00; N, 11.11% Found: C, 56.97; H, 3.81; N, 11.19% |

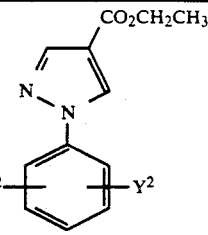

| PREP-ARA-TION | $X^2$ | $Y^2$ | m.p. (°C.) | Analysis |
|---|---|---|---|---|
| L | 3-Cl | 4-Cl | 140–42 (ethanol) | Calc'd For: $C_{12}H_{10}Cl_2N_2O_2$: C, 50.55; H, 3.54; N, 9.83% Found: C, 50.49; H, 3.31; N, 9.80% |

PREPARATION M 1-(4-Methoxyphenyl)-4-pyrazolecarboxylic acid

A stirred suspension of 4.10 g (16.65 mmole) of ethyl 1-(4-methoxyphenyl)-4-pyrazolecarboxylate (Beck, J. et al., J. Heterocyclic Chem., 24, 267 (1987)) in 65 ml of 2N sodium hydroxide was diluted with 5 ml of ethanol and warmed to 90° C. for fifteen minutes, cooled to room temperature and acidified to pH 2 with concentrated hydrochloric acid. Filtration and drying of the precipitated product furnished 3.40 g (94% yield) of white solid. The sample was recrystallized from ethanol, m.p. 235–7° C.

Analysis: Calculated for $C_{11}H_{10}N_2O_3$: C, 60.54; H, 4.62; N, 12.84%. Found: C, 60.50; H, 4.40; N, 12.77%

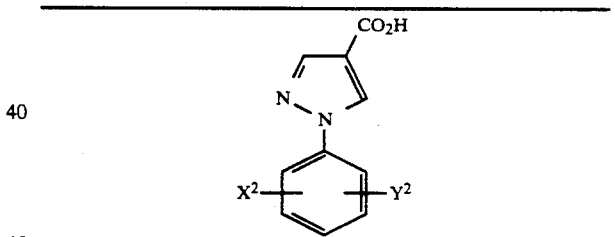

| PREP-ARA-TION | $X^2$ | $Y^2$ | m.p. (°C.) | Analysis |
|---|---|---|---|---|
| N | H | 4-Cl | 234–36 (ethyl acetate) | Calc'd For: $C_{10}H_7ClN_2O_2$: C, 53.94; H, 3.17; N, 12.59% Found: C, 53.97; H, 2.92; N, 12.54% |
| O | H | 4-F | 243–45 (ethanol) | Calc'd For: $C_{10}H_7FN_2O_2$: C, 58.25; H, 3.42; N, 13.59% Found: C, 58.08; H, 3.23; N, 13.52% |
| P | H | 3-F | 206–8 (acetonitrile) | Calc'd For: $C_{10}H_7FN_2O_2$: C, 58.25; H, 3.42; N, 13.59% Found: C, 58.19; H, 3.05; N, 13.50% |
| Q | 2-F | 5-F | 241–43 (ethanol) | Calc'd For: $C_{10}H_6F_2N_2O_2$: C, 53.58; H, 2.70; N, 12.50% Found: C, 53.34; H, 2.50; N, 12.34% |
| R | 2-F | 4-F | 230–32 (ethanol) | Calc'd For: $C_{10}H_6F_2N_2O_2$: C, 53.58; H, 2.70; N, 12.50% Found: C, 53.46; H, 2.45; N, 12.51% |
| S | H | 4-Br | 255–57 (ethanol) | Calc'd For: $C_{10}H_7BrN_2O_2$: C, 44.96; H, 2.64; N, 10.49% Found: C, 44.83; H, 2.47; N, 10.32% |
| T | 3-Cl | 4-Cl | 255–57 | Calc'd For: $C_{10}H_6Cl_2N_2O_2$: |

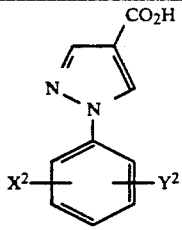

| PREPARATION | $X^2$ | $Y^2$ | m.p. (°C.) | Analysis |
|---|---|---|---|---|
| | | | (ethanol) | C, 46.72; H, 2.35; N, 10.90%<br>Found: C, 46.57; H, 2.17;<br>N, 10.81% |

What is claimed is:

1. A compound of the formula

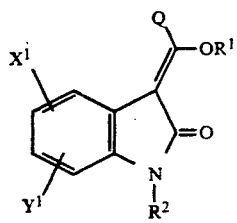

and pharmaceutically-acceptable salts thereof wherein

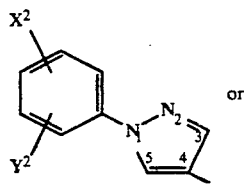

Q is $X^1$ is H, F, Cl, Br, $(C_1-C_6)$alkyl, $NO_2$, $CF_3$, CN, $S(O)_mR^3$, $OR^4$, $COR^4$ or $CONR^4R^5$;

$Y^1$ is H, F, Cl, Br, $(C_1-C_6)$alkyl, $NO_2$, $CF_3$, CN $S(O)_nR^6$, $OR^7$, $COR^7$, or $CONR^7R^8$;

$X^2$ is H, F, Cl, Br, $(C_1-C_4)$alkyl, $S(O)_pR^9$, $NO_2$, $COR^9$, $CONR^9R^{10}$, CN or $CF_3$;

$Y^2$ is H, F, Cl, Br, $(C_1-C_4)$alkyl, $S(O)_qR^{11}$, $NO_2$, $COR^{11}$, $CONR^{11}R^{12}$, CN or $CF_3$;

m and n are each zero, one or two; p and q are each one or two;

$R^1$ is H, alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omegaalkoxycarbonylalkanoyl, said alkoxy having one to three carbon atoms and said alkanoyl having three to five carbon atoms, alkoxy carbonyl of two to ten carbon atoms, phenoxycarbonyl, 1-(acyloxy)alkyl wherein acyl has one to four carbon atoms and said alkyl has two to four carbon atoms, 1-(alkoxycarbonyloxy)alkyl wherein said alkoxy has two to five carbon atoms and said alkyl has one to four carbon atoms, alkyl of one to three carbon atoms, alkylsulfonyl of one to three carbon atoms, methylphenylsulfonyl or dialkylphosphonate wherein each of said alkyl is one to three carbon atoms;

$R^2$ is $COR^{13}$, $CONR^{14}R^{15}$ or $(C_1-C_6)$alkyl;

$R^3$, $R^4$, $R^5$, $R^6$, $R^7$, $R^8$, $R^9$, $R^{10}$, $R^{11}$, $R^{12}$, $R^{14}$ and $R^{15}$ are each H or $(C_1-C_6)$alkyl; and $R^{13}$ is $(C_1-C_6)$alkyl.

2. A compound or a pharmaceutically-acceptable salt thereof according to claim 1 wherein $R^1$ is H.

3. A compound or a pharmaceutically-acceptable salt thereof according to claim 1 wherein $R^2$ is $CONR^{14}R^{15}$ and $R^{14}$ and $R^{15}$ are each H.

4. A compound or a pharmaceutically-acceptable salt thereof according to claim 3 wherein $R^1$ is H.

5. A compound or a pharmaceutically-acceptable salt thereof according to claim 1 wherein $X^2$ is H or F and $Y^2$ is H or F.

6. A compound or a pharmaceutically-acceptable salt thereof according to claim 1 wherein $X^1$ is H, F, Cl or CF and $Y^1$ is H or Cl.

7. A compound or a pharmaceutically-acceptable salt thereof according to claim 3 wherein Q is

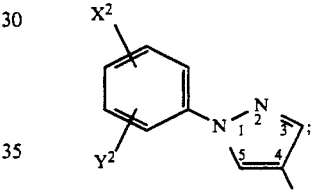

$X^1$ is H 5-F 5-Cl or 5-CF ; $Y^1$ is H or 6-Cl; $X^2$ is H or F; and $Y^2$ is H or F.

8. A compound or a pharmaceutically-acceptable salt thereof according to claim 4 wherein Q is

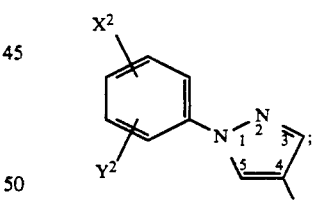

$X^1$ is H, 5-F 5-Cl or 5-$CF_3$; $Y^1$ is H or Cl; $X^2$ is H or F; and $Y^2$ is H or F.

9. A method of eliciting an analgesic response in a mammal which comprises administering to said mammal an analgesic response eliciting amount of a compound according to claim 1.

10. A method of treating an inflammatory disease in a mammal which comprises administering to said mammal an inflammatory disease treating amount of a compound according to claim 1.

11. The method according to claim 10 wherein the inflammatory disease is rheumatoid arthritis.

12. The method according to claim 10 wherein the inflammatory disease is osteoarthritis.

13. The method according to claim 10 wherein the inflammatory disease is psoriasis.

14. A pharmaceutical composition useful as an analgesic agent in a mammal which comprises a pharmaceutically-acceptable carrier and an analgesic response eliciting amount of a compound according to claim 1.

15. A pharmaceutical composition useful as an antiinflammatory agent in a mammal which comprises a pharmaceutically-acceptable carrier and an inflammatory disease treating amount of a compound according to claim 1.

16. A method of inhibiting prostaglandin $H_2$ synthase in a mammal in need thereof which comprises administering to said mammal a prostaglandin $H_2$ synthase inhibiting amount of a compound according to claim 1.

17. A method of inhibiting interleukin-1 biosynthesis in a mammal in need thereof which
comprises administering to said mammal an interleukin-1 biosynthesis inhibiting amount of a compound according to claim 1.

18. A method of treating interleukin-1 mediated bone metabolism disorders in a mammal which comprises administering to said mammal an interleukin-1 mediated bone metabolism disorder treating amount of a compound according to claim 1.

19. The method according to claim 18 wherein the bone metabolism disorder is osteoporosis.

20. A method of treating interleukin-1 mediated connective tissue metabolism disorder in a mammal which comprises administering to said mammal an interleukin-1 mediated connective tissue metabolism disorder treating amount of a compound according to claim 1.

21. The method according to claim 20 wherein the connective tissue metabolism disorder is periodontal disease or tissue scarring.

22. A method of treating interleukin-1 mediated immune dysfunction in a mammal which comprises administering to said mammal an interleukin-1 mediated immune dysfunction treating amount of a compound according to claim 1.

23. The method according to claim 22 wherein the immune dysfunction is allergy or psoriasis.

24. A pharmaceutical composition useful as an inhibitor of prostaglandin $H_2$ synthase in a mammal which comprises a pharmaceutically-acceptable carrier and a prostaglandin $H_2$ synthase inhibiting amount of a compound according to claim 1.

25. A pharmaceutical composition useful as an inhibitor of interleukin-1 biosynthesis in a mammal which comprises a pharmaceutically-acceptable carrier and an interleukin-1 biosynthesis inhibiting amount of a compound according to claim 1.

26. A pharmaceutical composition useful in treating interleukin-1 mediated bone metabolism disorder in a mammal which comprises a pharmaceutically-acceptable carrier and an interleukin-1 mediated bone metabolism disorder treating amount of a compound according to claim 1.

27. A pharmaceutical composition useful in treating interleukin-1 mediated connective tissue metabolism disorder in a mammal which comprises a pharmaceutically-acceptable carrier and an interleukin-1 mediated connective tissue metabolism disorder treating amount of a compound according to claim 1.

28. A pharmaceutical composition useful in treating interleukin-1 mediated immune dysfunction in a mammal which comprises a pharmaceutically-acceptable carrier and an interleukin-1 mediated immune dysfunction treating amount of a compound according to claim 1.

* * * * *

UNITED STATES PATENT AND TRADEMARK OFFICE
CERTIFICATE OF CORRECTION

PATENT NO. : 5,064,851

DATED : November 12, 1991

INVENTOR(S) : Carl J. Goddard et al.

It is certified that error appears in the above-identified patent and that said Letters Patent is hereby corrected as shown below:

At Column 1, line 47, "(C cycloalkenyl," should read
-- $(C_4-C_7)$ cycloalkenyl, --;

At Column 3, line 55, " 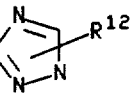 " should read

--  --;

At Column 4, line 3, "Col," should read -- Cl, --;

At Column 8, line 22, "$CONR^9,R^{10}$," should read -- $CONR^9R^{10}$, --;

At Column 8, line 48, "$CONR^9,R^{10}$," should read -- $CONR^9R^{10}$, --;

At Column 12, line 7, "agents" should read -- agent --;

At Column 13, line 11, after "secondary" should be inserted
-- amines, such as diethylamine, diethanolamine,
N-methyl- --;

At Column 14, line 5, "IL-1o" should read -- IL-1α --;

At Column 14, line 28, "i0" should be deleted;

At Column 14, line 50, "6 cells/ml. Then a 0.25 ml aliquot" should be deleted;

UNITED STATES PATENT AND TRADEMARK OFFICE
CERTIFICATE OF CORRECTION

PATENT NO. : 5,064,851
DATED : November 12, 1991
INVENTOR(S) : Carl J. Goddard et al.

It is certified that error appears in the above-identified patent and that said Letters Patent is hereby corrected as shown below:

At Column 18, line 6, the following should be inserted:

-- EXAMPLES 2-3

Employing procedures analogous to the procedure described in Example 1, above, with the appropriate substituted pyrazole-carboxylic acid and oxindole-1-carboxamide resulted in the preparation of the following compounds of the general formula shown.--;

At Column 19, line 1, the following should be inserted:

-- EXAMPLES 5-13

Employing procedures analogous to the procedure described in Example 4, above, with the appropriate acid and oxindole-1-carboxamide resulted in the preparation of the following compounds of the general formula shown.--;

At Column 20, line 54, the following should be inserted:

-- PREPARATIONS B-F

Employing procedures analogous to the procedure described in Preparation A, above, with the appropriate substituted phenylhydrazine hydrochloride resulted in the preparation of the following compounds of the general formula shown.--;

UNITED STATES PATENT AND TRADEMARK OFFICE
CERTIFICATE OF CORRECTION

PATENT NO. : 5,064,851

DATED : November 12, 1991

INVENTOR(S) : Carl J. Goddard et al.

It is certified that error appears in the above-identified patent and that said Letters Patent is hereby corrected as shown below:

At Column 21, line 42, the following should be inserted:

-- PREPARATIONS H-L

Employing procedures analogous to the procedure described in Preparation G, above, with the compounds prepared as described in Preparations B-F, above, resulted in the preparation following the compounds of the general formula shown.--;

At Column 22, line 35, the following should be inserted:

-- PREPARATIONS N-T

Employing procedures analogous to the procedure described in Preparation M, above, with the appropriate ester resulted in the preparation following the compounds of the general formula shown.--;

UNITED STATES PATENT AND TRADEMARK OFFICE
CERTIFICATE OF CORRECTION

PATENT NO.   : 5,064,851

DATED        : November 12, 1991

INVENTOR(S)  : Carl J. Goddard et al.

It is certified that error appears in the above-identified patent and that said Letters Patent is hereby corrected as shown below:

At Column 24, line 25, "CF" should read -- $CF_3$ --; and

At Column 24, line 38, "H 5-F 5-Cl or 5-CF;" should read -- H, 5-F, 5-Cl or 5-$CF_3$; --.

Signed and Sealed this

Twentieth Day of July, 1993

Attest:

MICHAEL K. KIRK

*Attesting Officer*   Acting Commissioner of Patents and Trademarks